United States Patent
Bolton et al.

(10) Patent No.: US 8,686,212 B2
(45) Date of Patent: Apr. 1, 2014

(54) PROCESS FOR TREATMENT OF ETHYLENE

(75) Inventors: Leslie William Bolton, Fleet (GB);
Benjamin Patrick Gracey, Hull (GB);
Michael Keith Lee, York (GB)

(73) Assignee: BP P.L.C., London (GB)

( * ) Notice: Subject to any disclaimer, the term of this patent is extended or adjusted under 35 U.S.C. 154(b) by 61 days.

(21) Appl. No.: 13/389,387

(22) PCT Filed: Aug. 10, 2010

(86) PCT No.: PCT/GB2010/001515
§ 371 (c)(1),
(2), (4) Date: Feb. 7, 2012

(87) PCT Pub. No.: WO2011/018619
PCT Pub. Date: Feb. 17, 2011

(65) Prior Publication Data
US 2012/0136192 A1    May 31, 2012

(30) Foreign Application Priority Data

Aug. 12, 2009 (EP) .................................. 09251984

(51) Int. Cl.
*C07C 7/00* (2006.01)
(52) U.S. Cl.
USPC ........................ 585/866; 585/809; 585/833
(58) Field of Classification Search
USPC ......... 585/639, 640, 809, 833, 864, 866, 867
See application file for complete search history.

(56) References Cited

U.S. PATENT DOCUMENTS

| | | |
|---|---|---|
| 5,603,835 A | 2/1997 | Cheung et al. |
| 5,817,906 A | 10/1998 | Marker et al. |
| 6,284,217 B1 | 9/2001 | Wang et al. |
| 6,300,433 B1 | 10/2001 | Rodriguez et al. |
| 6,659,248 B2 * | 12/2003 | Terada .................... 192/41 S |
| 6,844,480 B2 * | 1/2005 | Lattner et al. ................ 585/833 |
| 7,323,612 B2 * | 1/2008 | Egmond et al. ............... 585/809 |
| 2006/0111601 A1 | 5/2006 | Cheng et al. |
| 2009/0082605 A1 * | 3/2009 | Bailey et al. .................. 585/639 |

FOREIGN PATENT DOCUMENTS

| | | |
|---|---|---|
| EP | 1 888 492 | 7/1986 |
| EP | 0 303 438 A2 | 2/1989 |
| EP | 1 792 885 A1 | 6/2007 |
| EP | 1 899 284 | 3/2008 |
| EP | 1 902 006 | 3/2008 |
| EP | 1 904 423 | 4/2008 |
| EP | 1 904 426 | 4/2008 |

(Continued)

OTHER PUBLICATIONS

Linthwaite, M., et al; "Compact reformers in gas conversion"; *Hydrocarbon Engineering*; vol. 5, No. 5, pp. 67-69 (2000).

(Continued)

*Primary Examiner* — Walter D Griffin
*Assistant Examiner* — Jelitza Perez
(74) *Attorney, Agent, or Firm* — Nixon & Vanderhye P.C.

(57) ABSTRACT

Process for removing water from an ethylene stream containing water, by introducing an ethylene stream containing water into, and circulating the ethylene stream through, a separation vessel. A liquid diethyl ether stream is introduced into, and circulated through, the separation vessel so that the liquid diethyl ether stream and the ethylene stream containing water are brought into contact, and an ethylene stream having a reduced water content is recovered from the separation vessel.

16 Claims, 1 Drawing Sheet

(56) References Cited

FOREIGN PATENT DOCUMENTS

| | | |
|---|---|---|
| EP | 1 914 219 A1 | 4/2008 |
| EP | 1 923 380 A1 | 5/2008 |
| EP | 1 925 363 A1 | 5/2008 |
| EP | 1 954 654 | 8/2008 |
| EP | 1 954 655 | 8/2008 |
| EP | 1 954 656 | 8/2008 |
| EP | 1 954 657 | 8/2008 |
| EP | 2 021 310 | 2/2009 |
| EP | 2 024 315 | 3/2009 |
| EP | 2 060 553 A1 | 5/2009 |
| EP | 2 060 555 A1 | 5/2009 |
| EP | 2 072 488 A1 | 6/2009 |
| EP | 2 089 156 | 8/2009 |
| WO | WO 00/23689 | 1/1999 |
| WO | WO 99/02254 A1 | 1/1999 |
| WO | WO 2000/23689 | 4/2000 |
| WO | WO 2006/123158 A2 | 11/2006 |
| WO | WO 2007/003899 A1 | 1/2007 |
| WO | WO 2007/003901 A1 | 1/2007 |
| WO | WO 2007/003910 A1 | 1/2007 |
| WO | WO 2007/0039089 A1 | 1/2007 |
| WO | WO 2007/063279 A1 | 6/2007 |
| WO | WO 2007/063280 A1 | 6/2007 |
| WO | WO2007/063281 A1 | 6/2007 |
| WO | WO 2007/063282 A2 | 6/2007 |
| WO | WO 2007/138300 A1 | 12/2007 |
| WO | WO 2007/138303 A1 | 12/2007 |
| WO | WO 2008/047103 A1 | 4/2008 |
| WO | WO 2008/062157 A1 | 5/2008 |
| WO | WO 2008/138775 A1 | 11/2008 |
| WO | WO 2009/050433 A1 | 4/2009 |
| WO | WO 2009/063173 A1 | 5/2009 |
| WO | WO 2009/063174 A1 | 5/2009 |
| WO | WO 2009/063176 A1 | 5/2009 |
| WO | WO 2009/074774 A2 | 6/2009 |
| WO | WO 2009/077719 A1 | 6/2009 |
| WO | WO 2009/077720 A1 | 6/2009 |
| WO | WO 2009/077723 A1 | 6/2009 |
| WO | WO 2009/077726 A1 | 6/2009 |
| WO | WO 2009/077729 A1 | 6/2009 |
| WO | WO 2009/077730 A1 | 6/2009 |

OTHER PUBLICATIONS

*Today's Refinery*; vol. 15, No. 8, p. 9 (Aug. 2000).
Cesar, Marcos A. Nogueira; "Chemicals from Ethanol"; SRI Consulting (Menlo Park, California 94025), *Consulting Report PEP235, Process Economics Report 235*, 204 pgs. (Nov. 2007).
"Hydrocarbon Processing"; vol. 78, No. 4, pp. 87-90, 92-93 (Apr. 1999).
"Petrole et Techniques"; No. 415, pp. 86-93 (Jul.-Aug. 1998).
"IMRET 3: Proceedings of the Third International Conference on Microreaction Technology"; Editor W.Ehrfeld, springer Verlag, pp. 187-196 (1999).
"Hydrocarbon Engineering"; vol. 5, No. 5, pp. 67-69 (2000).
"Hydrocarbon Processing"; vol. 79, No. 9, p. 34 (Sep. 2000).
"Today's Refinery"; vol. 15, No. 8, p. 9 (Aug. 2000).
"SRI Consulting" (Menlo Park, California 94025), Consulting Report PEP235, Process Economics Report 235, Chemicals from Ethanol (Nov. 2007).
Gunardson, H.H., et al; "Produce CO-rich synthesis gas"; *Hydrocarbon Processing*; vol. 78, No. 4, pp. 87-90, 92-93 (Apr. 1999).
Bourbonneux, G.; "Fisher-Tropsch synthesis gas production routes"; *Petrole et Techniques*; No. 415, pp. 86-93 (Jul.-Aug. 1998).
Mayer, J., et al; "A Microstructured Reactor for the Catalytic Partial Oxidation of Methane to Syngas"; *IMRET 3: Proceedings of the Third International Conference on Microreaction Technology*; Editor W.Ehrfeld, Springer Verlag, pp. 187-196 (1999).
"Custom catalyst converts natural gas into liquids"; "Major player invests in GTL technology"; *Hydrocarbon Processing*; vol. 79, No. 9, p. 34 (Sep. 2000).

* cited by examiner

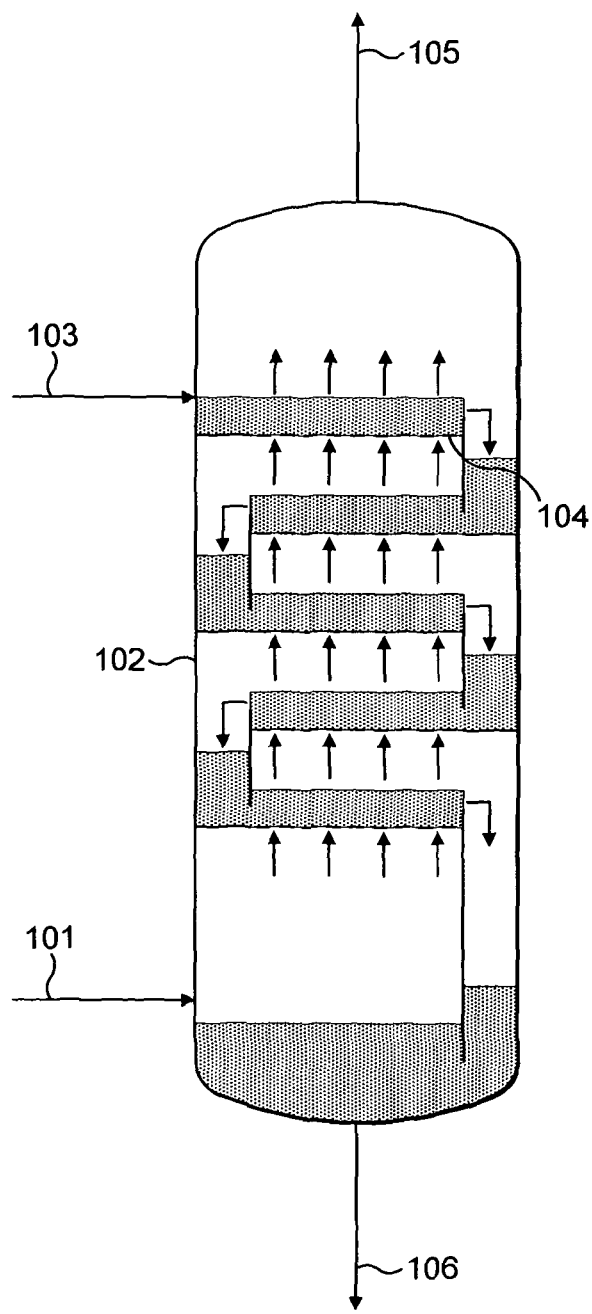

PROCESS FOR TREATMENT OF ETHYLENE

This application is the U.S. national phase of International Application No. PCT/GB2010/001515 filed 10 Aug. 2010 which designated the U.S. and claims priority to European Patent Application No. 09251984.2, filed 12 Aug. 2009, the entire contents of each of which are hereby incorporated by reference.

The present invention relates to a process for removing water from an ethylene stream comprising water.

More particularly, the present invention relates to a process for removing water from an ethylene stream comprising water using a liquid diethyl ether stream.

BACKGROUND OF THE INVENTION

Ethylene and other alkenes (also commonly referred to as olefins) are important commodity chemicals and are useful starting materials for numerous chemical products, including polymeric products, such as polyethylene. Traditionally, alkenes, such as ethylene, have been produced by steam or catalytic cracking of hydrocarbons derived from crude oil. However, as crude oil is a finite resource, there is interest in finding alternative, economically viable, methods for producing alkenes, in particular ethylene, which can use feedstocks not derived from crude oil.

In recent years the search for alternative materials for alkene production has led to the production of alkenes by the dehydration of alcohols, such as methanol and ethanol, which can be produced by the fermentation of, for example, sugars, starches and/or cellulosic materials, or alternatively may be produced from synthesis gas.

Examples of processes for the preparation of alkenes from alcohols include:

U.S. Pat. No. 5,817,906 discloses a process for producing light olefin(s) from a crude oxygenate feedstock comprising alcohol and water. The process employs two reaction stages. Firstly, the alcohol is converted, using reaction with distillation, to an ether. The ether is then subsequently passed to an oxygenate conversion zone containing a metalaluminosilicate catalyst to produce a light olefin stream.

EP 1792885 discloses a process for the production of ethylene from a feedstock comprising ethanol. Catalysts based on heteropolyacids are disclosed as being suitable for the dehydration of the ethanol feedstock.

WO 2008/138775 A1 discloses a process for the dehydration of one or more alcohols, which process comprises contacting one or more alcohols in the presence of one or more ethers with a supported heteropolyacid catalyst.

Before ethylene is used in downstream industrial applications, e.g. ethylene polymerization, the ethylene stream is typically subjected to a purification procedure. A primary impurity that is typically required to be removed from an ethylene stream is water, which is formed as a by-product in the dehydration of alcohols. For example, only a very low water content, typically in the order of low ppm concentrations, in an alkene feed, in particular an ethylene feed, is generally considered as acceptable for use in the preparation of polymers by catalytic polymerization; this is because water can act as a catalyst poison in the polymerization process. There are also other reasons why it is desirable to remove water from alkene, in particular ethylene, streams. For example, an ethylene stream may be utilised in downstream equipment which may be operated at very low temperatures, e.g. further purification of ethylene by distillation at, for example, −28° C.; at such low temperatures, any water present may freeze and could give rise to operational difficulties.

Different methods have been described in the prior art for the removal of water from ethylene. The use of molecular sieves is a known method for removing water (e.g. SRI Consulting (Menlo Park, Calif. 94025), Consulting Report PEP235, Process Economics Report 235, Chemicals from Ethanol, November 2007, describes that ethylene can be dried using a suitable desiccant such as a Type 3A molecular sieve); however, this method appears to be subject to several potential limitations and/or problems, such as:

it is a semi-batch operation,
ethylene may polymerise on the molecular sieve material,
it is very difficult to control the method to achieve the desired low levels of water content,
other organic components may be simultaneously caught on the molecular sieve material, and be either lost in regeneration or need expensive additional recovery methods, and
the molecular sieve separation method may cause a significant pressure drop which could increase the size of a downstream ethylene compressor, should one be required before the ethylene can be subjected to further downstream processing and/or use.

Thus, there exists a need for alternative methods for the removal of water from an ethylene stream.

SUMMARY OF THE INVENTION

It has been observed that the crude product compositions produced by dehydrating alcohols to produce alkenes can also contain significant quantities of ethers as well as by-product water. For example, the crude ethylene product produced from the dehydration of ethanol will typically comprise diethyl ether as well as the ethylene and water; depending upon the dehydration process used, the crude ethylene product may consist essentially of ethylene, diethyl ether and water.

It has unexpectedly been found that it is possible to use diethyl ether to reduce the water concentration of an ethylene stream comprising water.

Thus, the present invention provides a process for removing water from an ethylene stream comprising water, said process comprising:
introducing an ethylene stream comprising water into, and circulating said ethylene stream through, a separation vessel;
introducing a liquid diethyl ether stream into, and circulating said liquid diethyl ether stream through, the separation vessel, so that said liquid diethyl ether stream and said ethylene stream comprising water are brought into contact;
recovering an ethylene stream having a reduced water content from the separation vessel; and optionally
recovering a liquid diethyl ether stream having an increased water content from the separation vessel.

Beneficially, the process for removing water from an ethylene stream comprising water provided by the present invention can be used in a continuous manner.

Therefore, in a preferred embodiment of the process of the present invention there is provided a continuous process for removing water from an ethylene stream comprising water, said process comprising:
introducing an ethylene stream comprising water into, and circulating said ethylene stream through a separation vessel;

introducing a liquid diethyl ether stream into, and circulating said liquid diethyl ether stream through the separation vessel, so that said liquid diethyl ether stream and said ethylene stream comprising water are brought into contact;

recovering an ethylene stream having a reduced water content from the separation vessel; and recovering a liquid diethyl ether stream having an increased water content from the separation vessel.

FIG. 1 depicts a process for removing water from an ethylene stream comprising water, using a liquid diethyl ether stream which is externally sourced, in a distillation column employing sieve trays.

By the terms "remove water from the ethylene stream", "removing water from the ethylene stream", and the like, it is meant that at least part of the water present in the ethylene stream comprising water has been removed, i.e. the concentration of water in the ethylene stream is reduced.

Whilst not wishing to be bound by theory, it is believed that in the process of the present invention, an ethylene stream comprising water is brought into contact with a liquid diethyl ether stream and at least a portion of the water present in said ethylene stream is removed by the liquid diethyl ether stream by absorption to yield an ethylene stream having a reduced water content and a diethyl ether stream having an increased water content.

The process for removing water from an ethylene stream comprising water provided by the present invention may also be referred to herein as the scrubber process. The separation vessel in which the process for removing water from the ethylene stream comprising water provided by the present invention may also be referred to herein as the scrubber.

In the process of the present invention, the liquid diethyl ether stream is used to remove water from the ethylene stream comprising water to produce an ethylene stream having a reduced water content and a liquid diethyl ether stream having an increased water content, i.e. the liquid diethyl ether stream additionally comprising the water which has been removed from said ethylene stream. The liquid diethyl ether stream employed in the process of the present invention may also be referred to herein as the scrubbing feed.

The "ethylene stream comprising water" which is subjected to the process of the present invention is also be referred to herein as the "crude ethylene stream". Preferably, said crude ethylene stream comprises at least 60 wt % ethylene, more preferably at least 70 wt % ethylene, and more preferably at least 75 wt % ethylene, based on the total weight of the crude ethylene stream.

The amount of water present in the crude ethylene stream prior to introduction into the scrubber is typically less than 1.0 wt %, based on the total weight of the crude ethylene stream; preferably, the amount of water present in the crude ethylene stream prior to introduction into the scrubber is in the range of from 0.05 to 0.5 wt %, based on the total weight of the crude ethylene stream.

Depending upon the source of the crude ethylene stream, the crude ethylene stream may also contain diethyl ether in addition to ethylene and water.

Advantageously, it has been found that it is possible to use diethyl ether which may already be present in the ethylene stream comprising water as at least part of, preferably all of, the source of the liquid diethyl ether stream used to reduce the concentration of water in the crude ethylene stream in the process of the present invention.

Therefore, in one embodiment of the present invention, the ethylene stream comprising water which is subjected to the process of the present invention (i.e. the crude ethylene stream), is an ethylene stream comprising water and diethyl ether.

According to a preferred embodiment of the process of the present invention, before introduction in to the scrubber, the crude ethylene stream comprises enough diethyl ether for scrubbing the water present in said ethylene stream. In this embodiment of the process of the present invention, the crude ethylene stream preferably comprises at least 2 wt % of diethyl ether based on the total weight of the crude ethylene stream, more preferably at least 10 wt % of diethyl ether, and most preferably at least 15 wt % of diethyl ether.

According to a preferred embodiment of the process of the present invention, before introduction to the scrubber, the total amount of ethylene, water, and diethyl ether, in the crude ethylene stream is at least 95 wt %, more preferably at least 98 wt %, of the total weight of the crude ethylene stream. In one specific embodiment of the present invention, the total amount of ethylene, water, and diethyl ether, in the crude ethylene stream is 100 wt % of the total weight of the crude ethylene stream.

Compounds other than ethylene, water and diethyl ether, for example other oxygenates and/or alkanes, may also be tolerated in the crude ethylene stream; for example acetaldehyde and/or ethanol and/or dimethyl ether and/or ethane may also commonly be present in the crude ethylene stream. Typically, such other compounds which may be present in the crude ethylene stream will be present only in small amounts; preferably, the amount of compounds other than ethylene, water and diethyl ether present in the crude ethylene stream will be at most 5.0 wt % based on the total weight of the crude ethylene stream, more preferably at most 2.5 wt % based on the total weight of the crude ethylene stream, and even more preferably at most 1.0 wt % based on the total weight of the crude ethylene stream.

The ethylene stream comprising water which is to be subjected to the process of the present invention (i.e. the crude ethylene stream) is typically in a gaseous state prior to introduction to the scrubber. Preferably, the temperature and pressure of the crude ethylene stream before introduction to the scrubber are such that the water present in said crude ethylene stream does not freeze; more preferably, the temperature is at least 5° C. higher than the greater of the liquid freezing point and vapour reverse sublimation point of the water present at the respective pressure and composition of the crude ethylene stream.

The preferred pressure of the crude ethylene stream prior to introduction to the scrubber is at least 0.5 MPa, more preferably at least 1 MPa, and even more preferably at least 1.5 MPa; most preferably, the pressure of the crude ethylene stream prior to introduction to the scrubber is in the range of from 1.5 MPa to 3 MPa.

The preferred temperature of the crude ethylene stream prior to introduction to the scrubber is at least 0° C., more preferably at least 10° C., and even more preferably at least 15° C.; most preferably, the temperature of the crude ethylene stream prior to introduction to the scrubber is in the range of from 20 to 50° C.

The liquid diethyl ether stream that is introduced into the separation vessel may be introduced into the separation vessel in a liquid stream which is separate from the crude ethylene stream and/or may be formed within the separation vessel. If the liquid diethyl ether stream is formed within the separation vessel, then the diethyl ether may be introduced to the separation vessel within the crude ethylene stream or may be introduced to the separation vessel in a gaseous form independently from said crude ethylene stream.

In the embodiment of the present invention where the crude ethylene stream contains diethyl ether, at least a portion of said diethyl ether may conveniently be used as a source of diethyl ether for the liquid diethyl ether stream. In this embodiment, at least a portion of the diethyl ether present in the crude ethylene stream is condensed to form at least part of the liquid diethyl ether stream. In addition to the diethyl ether from the crude ethylene stream, additional diethyl ether may be introduced into the separation vessel to supplement the diethyl ether from the crude ethylene stream to form the liquid diethyl ether stream; said additional diethyl ether is most conveniently provided as a liquid diethyl ether stream that is introduced to the separation vessel from an external supply.

In addition to diethyl ether, the liquid diethyl ether stream may also contain other compounds. Preferably, the liquid diethyl ether stream will comprise at least 40 wt % diethyl ether, more preferably at least 50 wt % diethyl ether, even more preferably at least 60 wt % diethyl ether, based on the total weight of the liquid diethyl ether stream.

In a preferred embodiment of the process of the present invention, the liquid diethyl ether stream also contains a solvent which is used for suppressing the temperature of formation of hydrates of components which are, or may be, present in the crude ethylene stream (e.g. ethylene hydrate). Examples of solvents which may be used for suppressing the formation of hydrates of components present in the crude ethylene stream include ethanol, methanol, ethylene glycol, diethylene glycol, triethylene glycol, propylene glycol and glycerols. Therefore, in a particularly preferred embodiment of the process of the present invention, the liquid diethyl ether stream is a liquid diethyl ether stream comprising one or more solvent selected from ethanol, methanol and ethylene glycol.

In the above embodiment, said solvent(s) which may be used for suppressing the formation of hydrates of components present in the crude ethylene stream may be present in the liquid diethyl ether stream prior to introduction to the separation vessel or may be introduced to the separation vessel independently from the source of diethyl ether and combined with the diethyl ether within the separation vessel to form the liquid diethyl ether stream.

In the embodiment wherein the liquid diethyl ether stream comprises a solvent which may be used for suppressing the formation of hydrates of components present in the crude ethylene stream, said solvent is preferably present in an effective amount, i.e. an amount sufficient to suppress the formation of hydrates of components present in the crude ethylene stream under the conditions within the separation vessel. Typically, the amount of said solvent in the liquid diethyl ether stream is up to 60 wt % based on the total weight of the liquid diethyl ether stream, more preferably up to 40 wt % based on the total weight of the liquid diethyl ether stream, even more preferably in the range of from 1 wt % to 25 wt % based on the total weight of the liquid diethyl ether stream.

In the process of the present invention, the ethylene stream comprising water and the liquid diethyl ether stream are introduced into, and circulated through, a separation vessel so that said liquid diethyl ether stream and said ethylene stream comprising water are brought into contact.

The process of the present invention may be performed in any vessel suitable for contacting a liquid phase with a gaseous phase and for performing a phase separation. Such separation vessels may be single or multi-staged, and include, but are not limited to: flash vessels; and, distillation vessels; such as distillation columns employing sieve trays, valve trays, structured packing or random packing. Preferably the process of the present invention is performed in a multi-staged distillation column; more preferably the process of the present invention is performed in a separation vessel selected from: a multi-staged distillation column employing sieve trays; a multi-staged distillation column employing valve trays; multi-staged distillation column employing structured packing; and, multi-staged distillation column employing random packing.

If the separation vessel used in the process of the present invention is a multi-staged vessel, the number of ideal stages of separation in the separation vessel is at least 2, preferably at least 3; more preferably, the number of ideal stages of separation in the separation vessel is in the range of from 2 to 1000, more preferably in the range of from 2 to 500, even more preferably in the range of from 3 to 500, and most preferably in the range of from 3 to 400.

Whilst not wishing to be bound by this theory, it is believed that it is preferable to perform the process of the present invention in a multi-stage distillation vessel containing trays rather than packing, as low temperature operation of a separation vessel in the process of the present invention may give rise to liquid with surface tension high enough to potentially reduce the separation efficiency of structured or random packing. Therefore, in a particularly preferred embodiment, the separation vessel used in the process of the present invention is a multi-staged distillation column employing sieve trays or a multi-staged distillation column employing valve trays.

In one particular embodiment of the present invention, reflux may be provided to the separation vessel; i.e. by partial condensation of the overhead vapour of the separation vessel. The means for providing the reflux to the separation vessel may be an external heat transfer device connected to the separation vessel or may be a heat transfer device located within the actual separation vessel. Any suitable heat transfer device may be used to provide reflux to the separation vessel, including, but not limited to the following types of heat exchanger: shell and tube, including any means of extending the heat transfer surface of the tube; double tube; fin/fan; plate and frame compact of gasketed or welded manufacture; printed circuit; spiral-wound, falling film or spinning disc.

Cooling in the heat transfer device may preferably be effected by indirect heat transfer with a coolant, examples of which include, but are not limited to: ethylene and/or propylene glycol solution; propylene; ethylene; and, organic silica fluids. Additionally or alternatively, cooling in the heat transfer device may be effected by direct heat transfer, for example with an olefin.

When reflux is provided to the separation vessel, the liquid diethyl ether stream may conveniently be introduced to the separation vessel through the reflux, i.e. through the condensation of any diethyl ether that may be present in the gaseous phase within the separation vessel. For example, the liquid diethyl ether stream may be introduced to the separation vessel through reflux provided to the separation vessel by condensation of diethyl ether present in the crude ethylene stream.

Reflux may be augmented or replaced with a liquid stream containing the diethyl ether; whilst the source of the diethyl ether is not limited, said diethyl ether may conveniently be sourced from further separation of the gaseous and/or liquid effluent from the separation vessel. Such a stream may also or alternatively be introduced elsewhere in the column.

Preferably, the separation vessel in which the process of the present invention is performed is a separation vessel which comprises at least one inlet and at least two outlets. In the process of the present invention, the crude ethylene stream is introduced into the separation vessel through at least one inlet, an ethylene stream having a reduced water content is recovered through at least one outlet, and the liquid diethyl ether stream which has been circulated through the separation vessel is recovered through at least one outlet which is different to the outlet through which the ethylene stream having a reduced water content is recovered. The liquid diethyl ether stream that is introduced to the separation vessel may be formed within the separation vessel itself, may be introduced to the separation vessel through at least one additional inlet, or may be introduced into the separation vessel through the outlet from which the ethylene stream having a reduced water content is recovered.

Thus, in one particular embodiment of the process of the present invention, the separation vessel comprises at least two inlets and at least two outlets. In such an embodiment, the crude ethylene stream may be introduced through at least one inlet, a liquid diethyl ether stream may be introduced through at lest one inlet which is different to the inlet through which the crude ethylene is introduced, an ethylene stream having a reduced water content is recovered through at least one outlet, and the liquid diethyl ether stream which has been circulated through the separation vessel is recovered through at least one outlet which is different to the outlet through which the ethylene stream having a reduced water content is recovered.

In the embodiment wherein a solvent which may be used for suppressing the formation of hydrates of components present in the crude ethylene stream is introduced, the solvent which may be used for suppressing the formation of hydrates of components present in the crude ethylene stream may be introduced through the same inlet as the liquid diethyl ether stream (or the inlet through which the crude ethylene is introduced if the liquid diethyl ether stream is formed within the separation vessel), or through at least one additional inlet.

In the process of the present invention, the crude ethylene stream and the liquid diethyl ether stream are both, independently, circulated through the separation vessel. By circulated through the vessel, it is meant that the relevant stream is introduced (including introduction by formation/condensation) in one part of the separation vessel (e.g. an inlet and/or a condenser), said stream then is transported through the vessel to an outlet where it is removed from the separation vessel.

Preferably, in the process of the present invention, the liquid diethyl ether stream is circulated in a counter-current direction to the crude ethylene stream. By circulated in a counter-current direction, it is meant that the general direction of flow of each of the two streams, the crude ethylene stream and the liquid diethyl ether stream, is in opposing directions, e.g. one stream having an overall upward direction of flow and the other stream having an overall downward direction of flow.

Conveniently, the separation vessel used in the process of the present invention may be configured such that the crude ethylene stream may enter the separation vessel through an inlet located in the lower half of the separation vessel, said crude ethylene stream will then pass through the separation vessel in an upward direction and the ethylene stream having a reduced concentration of water is removed from the separation vessel through an outlet located in the upper half of the separation vessel. In such a configuration, the liquid diethyl ether stream would be introduced into the vessel in the upper half of the separation vessel, either through an inlet or through formation of the liquid diethyl ether stream by condensation within the separation vessel, the liquid diethyl ether stream will then pass through the vessel in a downward direction and said liquid diethyl ether stream is removed through an outlet located in the lower half of the separation vessel.

BRIEF DESCRIPTION OF THE DRAWINGS

A specific embodiment of the invention is described below with reference to the appended FIGURE which shows an embodiment of the process of the present invention. The appended FIGURE and accompanying description are not intended to restrict the scope of the invention to the specific embodiment described therein.

DETAILED DESCRIPTION OF THE INVENTION

FIG. 1 depicts one possible embodiment of the process of the present invention. In FIG. 1, an ethylene stream comprising water (101) enters a distillation column (102) through an inlet near the bottom of the column and rises through the column. Through an inlet near the top of the column, a liquid diethyl ether stream (103) enters the distillation column and descends through the column in a countercurrent direction to the ethylene stream. Within the distillation column there are arranged a number of sieve trays (104), the ethylene stream passes in an upward direction through the holes in said sieve trays and the liquid diethyl ether stream flows in a downwards direction through the "downcomers". From an outlet at the top of the distillation column, an ethylene stream having a reduced water content is recovered (105); and, from an outlet at the bottom of the distillation column, a liquid diethyl ether stream having an increased water content is removed (106).

Example

A distillation column, approximately 2650 mm high and 55 mm internal diameter, containing 11 PTFE sieve tray stages separated by glass downcomers of 90 mm length, 9 mm external diameter and approximately 7 mm internal diameter, was used in the following process.

A crude ethylene feed stream comprising ethylene saturated with diethyl ether, water and ethanol, was compressed and introduced to the distillation column below the bottom stage. The composition of the crude ethylene stream was approximately 89.40 mol % ethylene, 8.65 mol % diethyl ether, 0.57 mol % water and 1.38 mol % ethanol.

A vapour stream was removed from the top of the distillation column, from where it was fed to a partial condenser. The partial condenser provided a heat transfer area of approximately 34850 $mm^2$, to cool process contents to an exit temperature of approximately $-10°$ C. against a refrigerant with an entry temperature of approximately $-40°$ C.

The cooled stream from the partial condenser was passed to a pressure vessel, 2.4 liters in volume, which provided sufficient residence time for a liquid phase to separate from a gaseous phase. The liquid phase was continuously removed from the pressure vessel and fed back to the top stage of the distillation column as a reflux stream. To the reflux stream, ethanol was continuously injected.

An ethylene stream having reduced water content ("dried ethylene") was removed from the pressure vessel as the gaseous phase ("Heads" stream) and a liquid stream was removed from the base of the distillation column ("Base" stream).

The water content of the dried ethylene removed from the pressure vessel was measured using a dew point meter (AMT dew point transmitter, manufacturer by Alpha Moisture Systems, UK). Dew point readings from the analyser were converted to water content by predicting the water partial pressure at the measured dew point temperature (using the pure water vapour pressure model which is available in the sponsor release 2.3.0 of the DIPPR database).

The conditions and results from the above described process are provided in Tables 1, 2 and 3 below. The results were collected over a period of 123.5 hours of continuous operation.

TABLE 1

| | Flowrates | | | | Temperatures | | |
| --- | --- | --- | --- | --- | --- | --- | --- |
| | Column Feed (kg/hr) | Base (kg/hr) | Heads (kg/hr) | Ethanol injection (g/hr) | Column Feed (° C.) | Partial Condenser (° C.) | Pressure Column (barg) |
| Average | 3.34 | 1.31 | 2.03 | 62.32 | 42.53 | −9.96 | 19.43 |
| Standard Deviation | 0.15 | 0.05 | 0.16 | 0.43 | 0.69 | 0.36 | 0.19 |

TABLE 2

| | Feed Conditions | | |
| --- | --- | --- | --- |
| | Saturated temperature (° C.) | Saturated Pressure (barg) | Calculated Water Content of Feed (mmol/kmol) |
| Average | 45.0 | 15.8 | 5712 |
| Standard Deviation | 0.02 | 0.002 | n/a |

TABLE 3

| | Heads Analysis | |
| --- | --- | --- |
| | Measured Dew Point of Dried Ethylene Stream (° C.) | Calculated Water Content of Dried Ethylene Stream (mmol/kmol) |
| Average | −61.22 | 0.5 |
| Standard Deviation | 0.92 | n/a |

The invention claimed is:

1. A process for removing water from an ethylene stream comprising water, said process comprising:
   introducing an ethylene stream comprising water into, and circulating said ethylene stream through, a separation vessel;
   introducing a liquid diethyl ether stream into, and circulating said liquid diethyl ether stream through, the separation vessel, so that said liquid diethyl ether stream and said ethylene stream comprising water are brought into contact; and
   recovering an ethylene stream having a reduced water content from the separation vessel.

2. Process according to claim 1, wherein the process is operated in a continuous manner.

3. Process according to claim 1 or claim 2, wherein the ethylene stream comprising water comprises at least 60 wt % ethylene based on the total amount of the ethylene stream comprising water.

4. Process according to claim 1, wherein the amount of water present in the ethylene stream comprising water is less than 1.0 wt % based on the total weight of the ethylene stream comprising water.

5. Process according to claim 1, wherein the pressure of the ethylene stream comprising water before introduction to the separation vessel is at least 0.5 MPa.

6. Process according to claim 1, wherein the temperature of the ethylene stream comprising water before introduction to the separation vessel is at least 5° C. higher than the greater of the liquid freezing point and vapour reverse sublimation point of the water present at the respective pressure and composition of the crude ethylene stream.

7. Process according to claim 1, wherein the temperature of the ethylene stream comprising water before introduction to the separation vessel is at least 0° C.

8. Process according to claim 1, wherein the ethylene stream comprising water additionally comprises diethyl ether.

9. Process according to claim 8, wherein the ethylene stream comprises at least 2 wt % diethyl ether based on the total weight of the ethylene stream comprising water.

10. Process according to claim 8 or 9, wherein at least a portion of the diethyl ether present in the ethylene stream comprising water is used as a source of diethyl ether for the liquid diethyl ether stream.

11. Process according to claim 1, wherein the liquid diethyl ether stream comprises a solvent which is used for suppressing the temperature of formation of hydrates of components which may be present in the ethylene stream comprising water.

12. Process according to claim 11, wherein the liquid diethyl ether stream comprises one or more solvents selected from ethanol, methanol and ethylene glycol.

13. Process according to claim 11 or claim 12, wherein the solvent is introduced to the separation vessel independently from the source of diethyl ether and is combined with the diethyl ether within the separation vessel to form the liquid diethyl ether stream.

14. Process according to claim 1, wherein the separation vessel is a multi-staged distillation column.

15. Process according to claim 1, wherein reflux is provided to the separation vessel.

16. Process according to claim 1 further comprising recovering a liquid diethyl ether stream having an increased water content from the separation vessel.

* * * * *